(12) United States Patent
Sartawi

(10) Patent No.: US 11,950,775 B2
(45) Date of Patent: Apr. 9, 2024

(54) STITCHING METHOD FOR EVERTED WOUND CLOSURE

(71) Applicant: GIFTEDNESS AND CREATIVITY COMPANY, Safat (KW)

(72) Inventor: Muthana M. M. A. S. Sartawi, Safat (KW)

(73) Assignee: GIFTEDNESS AND CREATIVITY COMPANY, Safat (KW)

( * ) Notice: Subject to any disclaimer, the term of this patent is extended or adjusted under 35 U.S.C. 154(b) by 443 days.

(21) Appl. No.: 17/496,210

(22) Filed: Oct. 7, 2021

(65) Prior Publication Data

US 2022/0280154 A1 Sep. 8, 2022

Related U.S. Application Data

(63) Continuation-in-part of application No. 17/194,278, filed on Mar. 7, 2021, now abandoned.

(51) Int. Cl.
*A61B 17/06* (2006.01)

(52) U.S. Cl.
CPC .............. *A61B 17/06066* (2013.01); *A61B 2017/0608* (2013.01)

(58) Field of Classification Search
CPC ...... A61B 17/06066; A61B 2017/0608; A61B 17/04; A61B 17/0466
See application file for complete search history.

(56) References Cited

U.S. PATENT DOCUMENTS

| | | | |
|---|---|---|---|
| 5,053,047 A | 10/1991 | Yoon | |
| 5,433,728 A * | 7/1995 | Kim | A61B 17/06066 606/205 |
| 5,683,417 A | 11/1997 | Cooper | |
| 5,931,855 A | 8/1999 | Buncke | |
| 6,264,675 B1 | 7/2001 | Brotz | |
| 6,471,715 B1 | 10/2002 | Weiss | |
| 6,524,326 B1 * | 2/2003 | Zhu | A61B 17/0682 606/213 |
| 6,599,310 B2 | 7/2003 | Leung | |
| 7,875,043 B1 | 1/2011 | Ashby | |
| 8,211,126 B2 | 7/2012 | Yeh | |
| 8,292,920 B2 * | 10/2012 | Dabir | A61B 17/06066 606/222 |
| 8,506,594 B2 * | 8/2013 | AlGhamdi | A61B 17/06166 606/228 |

(Continued)

*Primary Examiner* — Phong Son H Dang
(74) *Attorney, Agent, or Firm* — Nath, Goldberg & Meyer; Richard C. Litman

(57) ABSTRACT

A stitching method for everted wound closure can include positioning a sutured needle on a first skin flap at a first side of the wound opening, inserting the sutured needle into the epidermis at the first side of the wound opening, passing the needle down through the dermis and toward the subcutaneous fat in either a curved or an acutely angled motion such that the suture forms, respectively, either a general C-shape or laboratory flask-like shape along a first side of the wound opening, and passing the sutured needle horizontally through the juncture or interface of the dermis/subcutaneous fat and back up through the dermis and epidermis toward the second skin flap at the second side of the wound opening in a similar and corresponding fashion as the first passage thereby completing the closure of the wound in a single pass.

4 Claims, 3 Drawing Sheets

(56) References Cited

U.S. PATENT DOCUMENTS

| | | | |
|---|---|---|---|
| 9,084,598 B2 | 7/2015 | Fedinec | |
| 9,706,983 B1* | 7/2017 | Alghamdi | A61B 17/06004 |
| 2002/0198565 A1 | 12/2002 | Dominguez | |
| 2003/0074023 A1 | 4/2003 | Kaplan | |
| 2004/0059377 A1 | 3/2004 | Peterson | |
| 2005/0182444 A1* | 8/2005 | Peterson | A61B 17/0644 |
| | | | 606/151 |
| 2009/0281569 A1 | 11/2009 | Alghamdi | |
| 2010/0217316 A1 | 8/2010 | Fedinec | |
| 2011/0077667 A1* | 3/2011 | Singhatat | A61B 17/0487 |
| | | | 606/228 |
| 2011/0264138 A1 | 10/2011 | Avelar | |
| 2012/0053603 A1 | 3/2012 | Williamson, IV | |
| 2013/0296930 A1* | 11/2013 | Belson | A61B 17/08 |
| | | | 606/215 |
| 2014/0128819 A1* | 5/2014 | Eaves | A61B 17/085 |
| | | | 606/213 |
| 2016/0278763 A1* | 9/2016 | Beaven Md | A61B 17/0482 |
| 2017/0014122 A1* | 1/2017 | Lear | A61B 17/0487 |
| 2017/0014124 A1* | 1/2017 | Lear | A61B 17/0487 |
| 2017/0071596 A1* | 3/2017 | Lear | A61B 17/08 |
| 2017/0303916 A1* | 10/2017 | Yuk | A61B 17/0469 |
| 2019/0321037 A1* | 10/2019 | Mitelberg | A61B 1/00137 |
| 2019/0336121 A1* | 11/2019 | Lear | A61B 17/0466 |
| 2019/0357908 A1* | 11/2019 | Luchetti | A61B 17/085 |
| 2022/0280154 A1* | 9/2022 | Sartawi | A61B 17/06066 |
| 2023/0181183 A1* | 6/2023 | Mitelberg | A61B 17/0625 |
| | | | 606/147 |

\* cited by examiner

STITCHING METHOD FOR EVERTED WOUND CLOSURE

CROSS REFERENCE TO RELATED APPLICATIONS

This application is a continuation-in-part of Ser. No. 17/194,278, filed Mar. 7, 2021, now pending.

BACKGROUND

1. Field

The disclosure of the present patent application relates to surgical methods, and particularly, to a surgical method for wound closure.

2. Description of the Related Art

The repair of many wounds is performed by the hand of a trained medical professional, often a surgeon. For both surgically or traumatically created full thickness wounds of the skin and subcutaneous tissues this has typically involved the layered repair of the subcutaneous portion (fat, superficial fascia, and deep dermis) of the wound as one layer and the upper dermis and epidermis as a second layer. Applying sutures to a wound using conventional methods can be associated with increased operating time. Longer operating times are associated with higher complication rates from both the anesthetic as well as higher risks of wound infection. Therefore, an efficient method of wound closure can improve outcomes.

Thus, a method for wound closure solving the aforementioned problems is desired.

SUMMARY

A stitching method for everted wound closure can include positioning a sutured needle on a first skin flap at a first side of the wound opening, inserting the sutured needle into the epidermis at the first side of the wound opening, passing the needle down through the dermis and toward the subcutaneous fat in a curved or semi-circular motion such that the suture forms a general C-shape along a first side of the wound opening, and passing the sutured needle horizontally through the subcutaneous fat and back up through the dermis and epidermis toward the second skin flap at the second side of the wound opening in a curved or semi-circular motion such that the suture forms a general C-shape along a second side of the wound opening.

Another stitching method for everted wound closure recognizes that the dermis layer can be classified as thin (about 1-4 mm) or thick (greater than 4 mm), wherein the passing of the suture needle through a thin dermis layer is at a small acute angle (about 10-30 degrees) that progressively increases (that is, the angle becomes more acute, about 30-60 degrees) as the dermis layer thickens. Furthermore, as the suture needle begins its horizontal passage toward the second skin flap at the second side of the wound opening, the medical practitioner ensures that the suture needle traverses along the juncture or interface of the dermis and subcutaneous fat layer. The purpose of this interfacial passage is to avoid gathering any subcutaneous fat in the closure of the wound. As in the first embodiment of the stitching method, the suture needle is pulled back up through the dermis and epidermis toward the second skin flap at the second side of the wound opening in a corresponding acute angled motion such that the suture forms a generally "laboratory flask-like" appearance.

These and other features of the present disclosure will become readily apparent upon further review of the following specification and drawings.

DETAILED DESCRIPTION OF THE PREFERRED EMBODIMENTS

Figure 1:
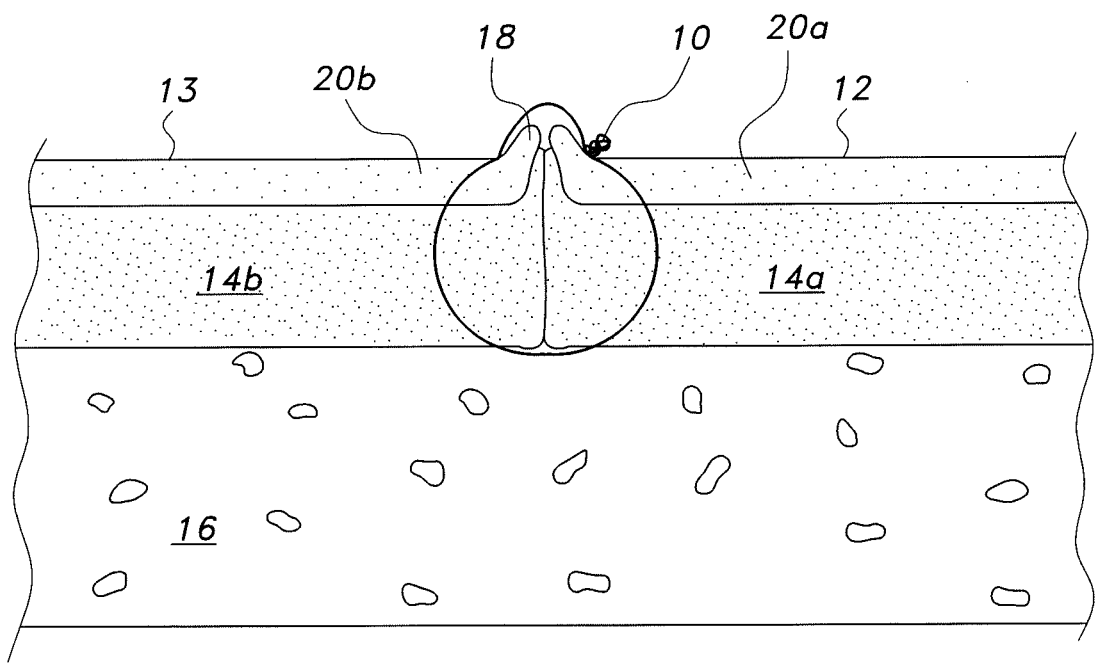
FIG. 1 is a schematic diagram of a first embodiment of an everted wound closure achieved by performing the method according to the present teachings.

Referring to FIG. 1, a stitching method for everted wound closure can include positioning a sutured needle on a first skin flap 12 at a first side of the wound opening, inserting the sutured needle into the epidermis 20a at the first side of the wound opening, passing the needle down through the dermis 14a and toward the subcutaneous fat 16 in a curved or semi-circular motion such that the suture forms a general C-shape along a first side of the wound opening, and passing the sutured needle horizontally through the subcutaneous fat and back up through the dermis 14b and epidermis 20b toward the second skin flap 13 at the second side of the wound opening in a curved or semi-circular motion such that the suture forms a general C-shape along the second side of the wound opening. When the suture is passed through the skin in this fashion and pulled tight, the larger dermis portion of the wound that is adjacent the subcutaneous fat is pulled together and pushed towards the epidermis, creating a skin eversion 18 or exposing a portion of the dermis 14a, 14b from both sides of the wound opening. The physician would close the wound by tying off the suture with knot 10. The present method can, thereby, evert the skin in a single pass of the suture or single insertion of the needle into the epidermis.

In the first embodiment as depicted in FIG. 1, the distance between the point at which the needle enters the first skin flap can be a first distance from the wound opening and the point at which the needle exits the second skin flap can be a second distance from the wound opening. In an embodiment, the first and second distances are the same. In an embodiment, the first and second distances are about one centimeter.

After piercing the epidermis at the first flap, the needle can be moved in a semi-circular motion through the dermis toward the subcutaneous fat layer. Then, the needle can be moved horizontally toward the second side of the wound opening through the subcutaneous fat layer and back through the dermis and out of the epidermis of the second flap in a semi-circular motion. In an embodiment, the suture forms a generally circular shape within the wound once the suture exits the second flap. Each half of the generally circular suture in the wound is preferably about the same size and shape. In an embodiment, the suture includes nylon.

Unlike prior stitching methods which require more than one pass of the suture needle through each wound edge to achieve everted wound closure, the present method can evert the skin in a single pass of the suture needle. Eversion facilitates proper approximation of wound edges and, thereby, expedited healing. As the present method only requires one pass of the suture needle through each skin flap, the present method is more efficient than prior stitching methods.

Figure 2:
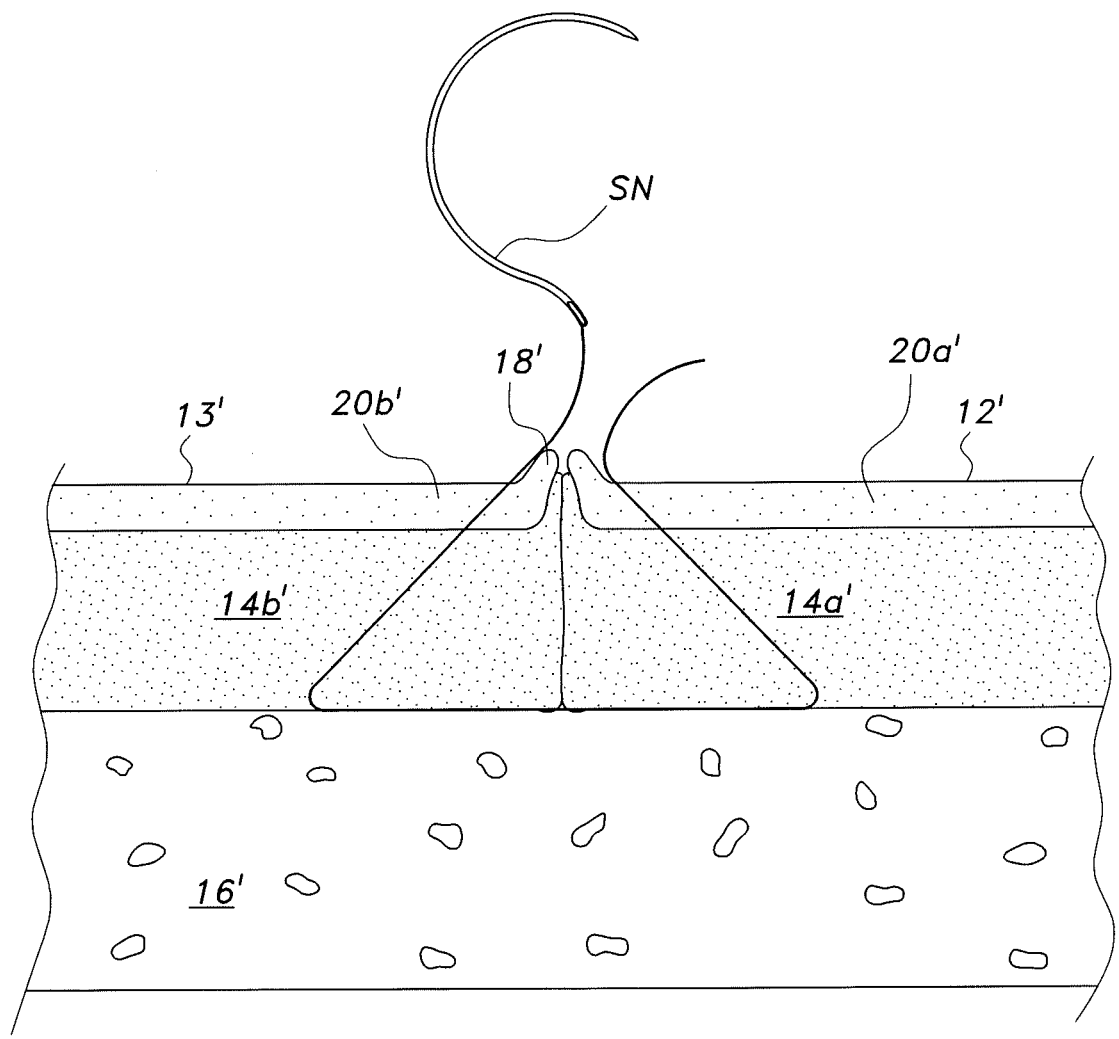
FIG. 2 is a schematic diagram of a second embodiment of an everted wound closure achieved by performing the method on a thin dermis layer according to the present teachings.
Figure 3:
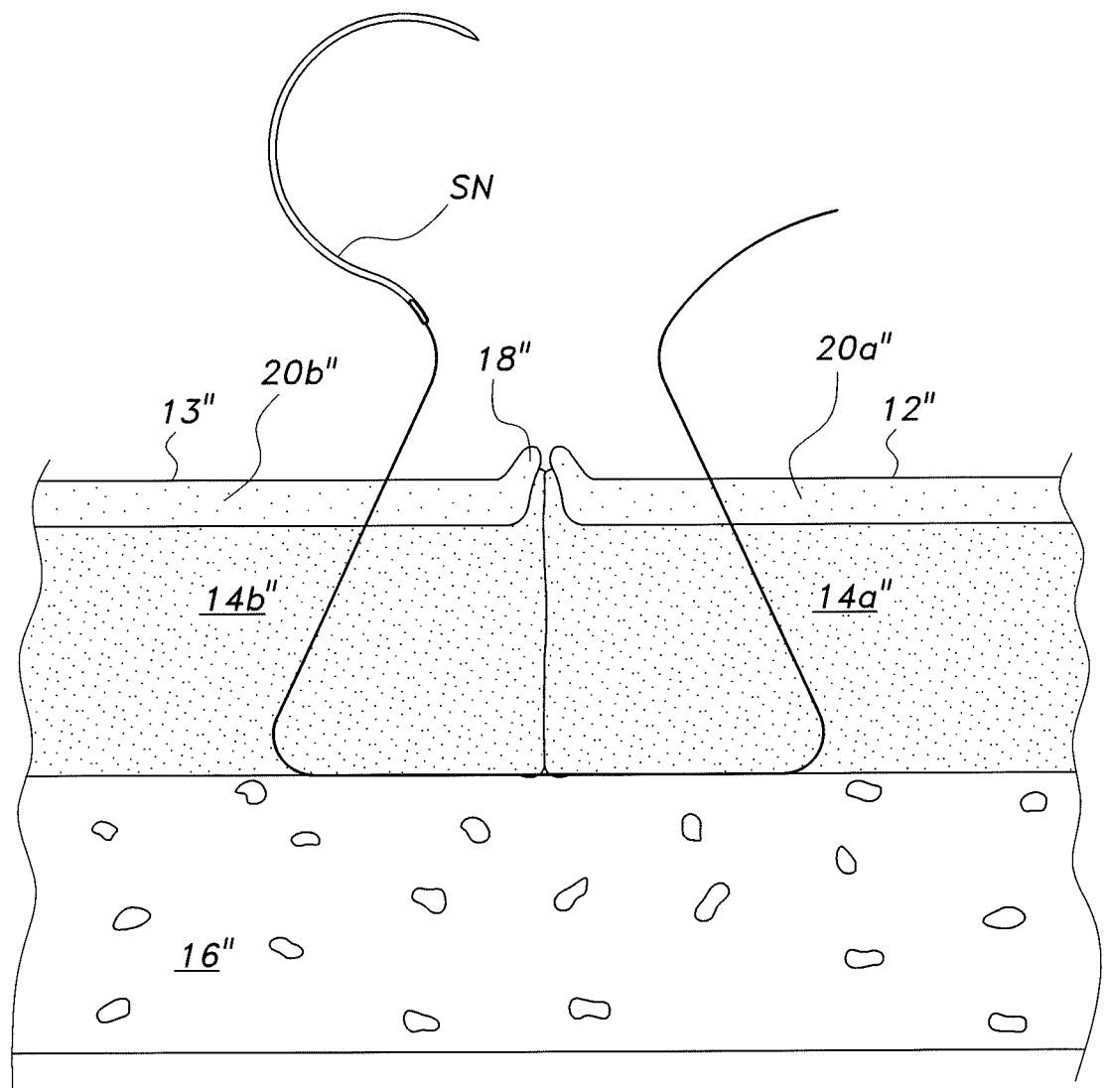
FIG. 3 is a schematic diagram of the second embodiment of an everted wound closure achieved by performing the method on a thick dermis layer according to the present teachings.

Referring to FIGS. 2 and 3, a second embodiment of the stitching method for everted wound closure is illustrated. In this stitching method for everted wound closure, the sutured needle SN is positioned on a first skin flap 12',12" at a first side of the wound opening, inserting the sutured needle into the epidermis 20a', 20a" at the first side of the wound opening, passing the needle down through the dermis 14a', 14a" at an acute angle and toward the subcutaneous fat 16',16" in such that the suture forms an acute angle along a first side of the wound opening, and passing the sutured needle horizontally through the junction or interface of the dermis and subcutaneous fat and back up through the dermis 14b',14b" and epidermis 20b',20b" toward the second skin flap 13',13" at the second side of the wound opening in a correspondingly acutely angled motion such that the suture forms a generally "laboratory flask-like" appearance. When the suture is passed through the skin in this fashion and pulled tight, the larger dermis portion of the wound that is adjacent the subcutaneous fat is pulled together and pushed towards the epidermis, creating a skin eversion 18',18" or exposing a portion of the dermis 14a', 14b" from both sides of the wound opening. The medical practitioner would close the wound by tying off the suture with a conventional knot. The present method can, thereby, evert the skin in a single pass of the suture or single insertion of the needle into the epidermis.

As depicted in FIGS. 2 and 3, a medical practitioner recognizes that the dermis layer can be classified as thin (about 1-4 mm) or thick (greater than 4 mm), wherein the passing of the sutured needle through a thin dermis layer is at a small acute angle (about 10-30 degrees) that progressively increases (that is, the angle becomes more acute, about 30-60 degrees) as the dermis layer thickens. Furthermore, as the sutured needle begins its horizontal passage toward the second skin flap at the second side of the wound opening, the medical practitioner ensures that the sutured needle traverses along the juncture or interface of the dermis and subcutaneous fat layer. The purpose of this interfacial passage is to avoid gathering any subcutaneous fat in the closure of the wound. As in the first embodiment of the stitching method, the suture needle is pulled back up through the dermis and epidermis toward the second skin flap at the second side of the wound opening in a corresponding acute angled motion such that the suture forms a generally "laboratory flask-like" appearance.

As in the first embodiment, the distance between the point at which the needle enters the first skin flap can be a first distance from the wound opening and the point at which the needle exits the second skin flap can be a second distance from the wound opening. As previously discussed, the first and second distances may be the same and may be about one centimeter.

Unlike prior stitching methods which require more than one pass of the sutured needle through each wound edge to achieve everted wound closure, the present method depicted in FIGS. 2 and 3 can evert the skin in a single pass of the sutured needle. Eversion facilitates proper approximation of wound edges and, thereby, expedited healing. The present method only requires one pass of the sutured needle through each skin flap, the present method is more efficient than prior stitching methods.

It is to be understood that the stitching method for everted wound closure is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A single pass stitching method for everted wound closure, comprising the steps of:

observing a wound opening;

noting the wound opening has a first skin flap on a first side of the wound opening and a second skin flap on a second side of the wound opening;

inserting a sutured needle into the epidermis of the first skin flap on the first side of the wound opening;

passing the sutured needle through the dermis and toward the subcutaneous fat at the first side of the wound opening in a first acutely angled motion;

passing the sutured needle from the dermis horizontally through the dermis/subcutaneous fat interface; and passing the sutured needle back from the dermis/subcutaneous fat interface through the dermis and out of the epidermis of the second skin flap in a second acutely angled motion on the second side of the wound opening, wherein the first and second acutely angled motions are equivalent, thereby ending the single pass stitching method for everted wound closure, whereby the suture forms a generally laboratory flask-like appearance within the wound after the sutured needle is pulled out of the second skin flap and the suture is knotted further including a step of observing the thickness of the dermis prior to inserting the sutured needle into the epidermis of the first skin flap on the first side of the wound opening; further including a step of determining thickness of the dermis as either 1-4 mm or greater than 4 mm; wherein the determination of the thickness of the dermis establishes the angulation of the first and second acutely angled suturing motion.

2. The stitching method for everted wound closure according to claim 1, wherein a distance between the point at which the needle enters the first skin flap and the wound opening and a distance between the point at which the needle exits the second skin flap the wound opening is the same distance.

3. The stitching method for everted wound closure according to claim 2, wherein the distance is one centimeter.

4. The stitching method for everted wound closure according to claim 1, wherein the suture comprises nylon.

* * * * *